United States Patent [19]

Hester, Jr. et al.

[11] Patent Number: 4,514,407
[45] Date of Patent: Apr. 30, 1985

[54] 1-ETHANAMINE-TRIAZOLO-BENZODIAZEPINES AS DIURETICS

[75] Inventors: Jackson B. Hester, Jr., Comstock Township, Kalamazoo County; James H. Ludens, Portage, both of Mich.

[73] Assignee: The Upjohn Company, Kalamazoo, Mich.

[21] Appl. No.: 476,181

[22] Filed: Mar. 17, 1983

[51] Int. Cl.³ ................ A61K 31/55; C07D 487/04
[52] U.S. Cl. ..................... 514/220; 260/239.3 D; 260/244.4; 260/245.5
[58] Field of Search ............... 260/245.5; 424/263, 424/269, 244, 246, 250, 251, 262

[56] References Cited

U.S. PATENT DOCUMENTS

| | | | |
|---|---|---|---|
| 3,759,943 | 9/1973 | Hester, Jr. | 260/245.5 |
| 3,767,661 | 10/1973 | Hester, Jr. | 260/244.4 |
| 3,969,504 | 7/1976 | Hester, Jr. | 424/244 |
| 3,987,052 | 10/1976 | Hester, Jr. | 260/245.5 |
| 3,994,940 | 11/1976 | Hester, Jr. | |
| 4,012,413 | 3/1977 | Hester, Jr. | 260/245.5 |
| 4,075,221 | 2/1978 | Hester, Jr. | 260/245.5 |
| 4,375,473 | 3/1983 | Rudzik | 424/269 |
| 4,455,307 | 6/1984 | Hester, Jr. | 424/269 |

OTHER PUBLICATIONS

*Physicians' Desk Reference* (PDR), 34th Edit. (1980), Publisher. Chas. E. Baker, Jr., pp. 216–217.
Roseberry et al, *Biometrics*, 20, (1964), pp. 73–84.

*Primary Examiner*—Alton D. Rollins
*Attorney, Agent, or Firm*—John T. Reynolds

[57] ABSTRACT

Triazolo-benzodiazepine-1-ethanamines of the formulas

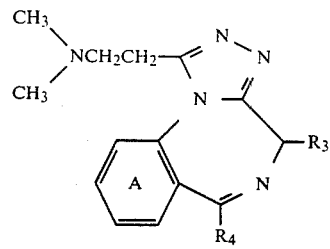

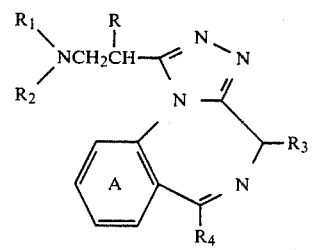

where R, $R_1$, $R_2$, $R_3$, $R_4$ and Ring A are as defined in the specification, e.g., 8-chloro-N,N-dimethyl-$\beta$,6-diphenyl-4H-[1,2,4]triazolo[4,3-a][1,4]benzodiazepine-1-ethanamine, and pharmacologically acceptable salts thereof, have been found to have substantial diuretic, natriuretic, but little, if any, kaliuretic activity, which can be used alone, or concomittently with other diuretic drugs such as furosemide or hydrochlorothiazide and/or with antihypertensive agents such as propranolo, captopril, minoxidil, prazosin, guanadrel sulfate, whose actions are supplemented by the action of a diuretic drug.

16 Claims, No Drawings

1-ETHANAMINE-TRIAZOLO-BENZODIAZE-PINES AS DIURETICS

INTRODUCTION

This invention relates to pharmaceutical compositions and methods of treating high blood pressure and other disease and abnormal conditions in valuable warm-blooded animals, including humans, in need of diuretic drug treatment using certain novel or known 4H-[1,2,4]triazolo[4,3-a][1,4]benzodiazepine-1-ethanamines. These compounds have been found to possess diuretic and natriuretic (sodium ion removing) properties but little, if any, kaliuretic (potassium ion removing) properties. Some of these compounds are new.

BACKGROUND OF THE INVENTION

In a variety of clinical (valuable warm-blooded animal and human treatment) situations, the presence of too much extracellular fluid in body tissues (edema) can be a problem in itself, or a problem which interferes with the treatment of other associated abnormal or disease conditions of concern to the patient and/or physician. Examples of clinical circumstances that can be associated with edema include congestive heart failure, advanced hepatic cirrhosis, nephrotic syndrome, and chronic renal failure.

Many diuretic drug compounds are known for treatment of edema and lists of various commercially available diuretics can be found in various publications, e.g., the *Physicians' Desk Reference* (PDR), 34th Edition (1980), published by Charles E. Baker, Jr., Copyright 1980 by Litton Industries, Inc., Published by Medical Economics Company, a Litton division at Oradell, NJ 07649, under DIURETICS on pp. 216-217 thereof. However, at least some of these known listed diuretic agents cause excretion of substantial amounts of potassium ions necessitating that care is taken to avoid the urinary elimination of too much potassium which is needed to maintain normal ion balance in the body.

In other clinical situations, blood pressure may be abnormally elevated for reasons known or unknown. Diuretic drug compounds, either because of their ability to remove extracellular fluid itself or because of some other pharmacological property, also frequently lower abnormally elevated blood pressure.

Moreover, some compounds which initially show promise as diuretic drugs are often later dropped from consideration as diuretic drugs because of toxicity or other undesired properties of the compounds.

Persons in the art concerned with the search for safe diuretic and natriuretic drugs continue to look for drugs which will effectively remove water and sodium ion without also depleting the potassium ion levels of the body to below acceptable levels.

OBJECTS OF THE INVENTION

It is an object of this invention to provide the medical, including the veterinary, profession with some diuretic drug compounds which help alleviate high blood pressure (hypertension) and excess body fluid conditions (edema) and which diuretic drug compounds have little, if any, effect on normal urinary potassium ion excretion rates.

It is another object of this invention to provide a process and pharmaceutical compositions for treating warm-blooded animals, including humans, suffering from high blood pressure (hypertension) and other disease or abnormal conditions, with diuretic drug compounds which are comparatively safe as a class and which minimize the urine excretion of potassium ions from the body.

It is also an object of this invention to provide, as new compounds, some triazolo-benzodiazepine-1-ethanamine derivative compounds, which are useful per se, or as their pharmacologically acceptable salts, as diuretic drugs.

Other objects, aspects and purposes of this invention will be apparent from reading the remaining specification and the claims which follow.

SUMMARY OF THE INVENTION

Briefly, according to this invention we have discovered that a small group of substituted triazolo-benzodiazepine-1-ethanamine compounds, e.g., 8-chloro-N,N-dimethyl-$\beta$,6-diphenyl-4H-[1,2,4]triazolo[4,3-a][1,4]benzodiazepine-1-ethanamine, and 8-iodo-N,N-dimethyl-$\beta$,6-diphenyl-4H-[1,2,4]triazolo[4,3-a][1,4]benzodiazepine-1-ethanamine and their pharmacologically acceptable salts, are active diuretic compounds which assist warm-blooded animal patients, including humans, in excreting water and sodium ions while minimizing the amount of potassium ion excreted. As a class these triazolo-benzodiazepine compounds possess little, if any, acute toxicity and they are compatible in their concommitent use with other diuretic agents such as furosemide or hydrochlorothiazide, and with their concommitent use with antihypertensive drugs such as propranolol, captopril, minoxidil, prazosin, guanadrel sulfate, and the like, whose actions are supplemented by the action of a diuretic drug.

DETAILED DESCRIPTION OF THE INVENTION

More particularly, this invention provides a process and pharmaceutical compositions for inducing diuresis in a warm-blooded animal patient which comprises administering to said patient a safe, non-toxic, effective amount of the compound of Formula I (See formulas below) wherein $R_3$ is hydrogen or $C_1$ to $C_3$-alkyl;

$R_4$ is phenyl or 1-, 3-, or 4-pyridinyl;

ring A is substituted by one or more fluorine, bromine, iodine, $C_1$ to $C_3$-alkyl, hydroxy, $C_1$ to $C_3$-alkyloxy, $C_1$ to $C_3$-alkylthio, amino, $C_1$ to $C_3$-alkylamino, di($C_1$ to $C_3$-alkyl)amino, trifluoromethyl, or nitro;

or of a compound of the Formula II (See formulas below) wherein

R is phenyl substituted by zero to 2 methoxy or ortho-chlorine groups;

$R_1$ and $R_2$ are independently hydrogen or $C_1$ to $C_3$-alkyl;

$R_3$ is hydrogen or $C_1$ to $C_3$-alkyl;

$R_4$ is phenyl or 2-, 3-, or 4-pyridinyl;

ring A is substituted by one or more fluorine, chlorine, bromine, iodine, $C_1$ to $C_3$-alkyl, hydroxy, $C_1$ to $C_3$-alkyloxy, $C_1$ to $C_3$-alkylthio, amino, $C_1$ to $C_3$-alkylamino, di($C_1$ to $C_3$-alkyl)amino, trifluoromethyl or nitro;

or a pharmaceutically acceptable salt thereof.

This invention also provides novel compounds of the Formula I (See formulas below) wherein $R_3$ is hydrogen or $C_1$ to $C_3$-alkyl;

$R_4$ is phenyl;

ring A is substituted by one or more iodine groups; or a pharmaceutically acceptable salt thereof.

Examples of such compounds include:

8-iodo-N,N-dimethyl-6-phenyl-4H-[1,2,4]triazolo[4,3-a][1,4]benzodiazepine-1-ethanamine, 8-iodo-N,N,4-trimethyl-6-phenyl-4H-[1,2,4]triazolo[4,3-a][1,4]benzodiazepine-1-ethanamine, and 8,9-diiodo-N,N-dimethyl-6-phenyl-4H-[1,2,4]triazolo[4,3-a][1,4]benzodiazepine-1-ethanamine.

The said novel compounds of this invention of the Formula I can be prepared by methods known in the art. For example, 7-iodo-1,3-dihydro-5-phenyl-2H-1,4-benzodiazepine-2-thione or its 3-methyl derivative (prepared by methods known in the art) is reacted with acetic acid hydrazide according to the method of Example 1 of Hester, Jr., U.S. Pat. No. 3,987,052. The resulting 8-iodo-1-methyl-6-phenyl-4H-[1,2,4]triazolo[4,3-a][1,4]benzodiazepine is reacted with a dimethylmethyleneammonium salt by the method of Hester, Jr., U.S. Pat. No. 4,075,221 to produce said novel compounds of this invention which are isolated and purified by conventional methods such as extraction, column chromatography, crystallization and the like. Alternatively, the methods described in Hester, Jr., U.S. Pat. No. 4,012,413 are used to produce the novel compounds of this invention of the Formula I.

This invention also provides novel compounds of the Formula II wherein

R is phenyl substituted by one to 2 substituents selected from the group consisting of methoxy in the meta or para position;

$R_1$ and $R_2$ are independently hydrogen or $C_1$ to $C_3$-alkyl;

$R_3$ is hydrogen or $C_1$ to $C_3$-alkyl;

$R_4$ is phenyl;

ring A is substituted by one or more fluorine, chlorine, bromine, $C_1$ to $C_3$-alkyl, hydroxy, $C_1$ to $C_3$-alkyloxy, $C_1$ to $C_3$-alkylthio, amino, $C_1$ to $C_3$-alkylamino, di($C_1$ to $C_3$-alkyl)amino, trifluoromethyl or nitro; PS or a pharmaceutically acceptable salt thereof.

Examples of such compounds include:

8-chloro-β-(3-methoxyphenyl)-N,N-dimethyl-6-phenyl-4H-[1,2,4]triazolo[4,3-a][1,4]benzodiazepine-1-ethanamine, 8-chloro-β-(4-methoxyphenyl)-N,N-dimethyl-6-phenyl-4H-[1,2,4]triazolo[4,3-a][1,4]benzodiazepine-1-ethanamine, 8-chloro-β-(3-methoxyphenyl)-N-methyl-6-phenyl-4H-[1,2,4]triazolo[4,3-a][1,4]benzodiazepine-1-ethanamine, 8-chloro-β-(3-methoxyphenyl)-6-phenyl-4H-[1,2,4]triazolo[4,3-a][1,4]benzodiazepine-1-ethanamine, 8-bromo-β-(4-methoxyphenyl)-N,4-dimethyl-6-phenyl-4H-[1,2,4]triazolo[4,3-a][1,4]benzodiazepine-1-ethanamine, and 8-methylthio-β-(3-methoxyphenyl)-N,N-dimethyl-6-phenyl-4H-[1,24]triazolo[4,3-a][1,4]benzodiazepine-1-ethanamine.

This invention also provides novel compounds of the Formula II wherein

R is phenyl;

$R_1$ is hydrogen and $R_2$ is hydrogen or $C_1$ to $C_3$-alkyl;

$R_3$ is hydrogen;

$R_4$ is phenyl;

ring A is substituted by one or more fluorine, chlorine, bromine, $C_1$ to $C_3$-alkyl, hydroxy, $C_1$ to $C_3$-alkyloxy, $C_1$ to $C_3$-alkylthio, amino, $C_1$ to $C_3$-alkylamino, di($C_1$ to $C_3$-alkyl)amino, trifluoromethyl or nitro;

or a pharmaceutically acceptable salt thereof.

Examples of such compounds include:

8-chloro-β,6-diphenyl-4H-[1,2,4]triazolo[4,3-a][1,4]benzodiazepine-1-ethanamine, 8-chloro-N-methyl-β,6-diphenyl-4H-[1,2,4]triazolo[4,3-a][1,4]benzodiazepine-1-ethanamine, 8-bromo-β,6-diphenyl-4H-[1,2,4]triazolo[4,3-a][1,4]benzodiazepine-1-ethanamine, 8-trifluoromethyl-N-ethyl-β,6-diphenyl-4H-[1,2,4]triazolo[4,3-a][1,4]benzodiazepine-1-ethanamine, 8-nitro-β,6-diphenyl-4H-[1,2,4]triazolo[4,3-a][1,4]benzodiazepine-1-ethanamine, and 8-methyl-N-(1-propyl)-β,6-diphenyl-4H[1,2,4]triazolo[4,3-a][1,4]benzodiazepine-1-ethanamine.

This invention also provides novel compounds of the Formula II wherein

R is phenyl;

$R_1$ and $R_2$ are independently hydrogen or $C_1$ to $C_3$-alkyl;

$R_3$ is $C_1$ to $C_3$-alkyl;

$R_4$ is phenyl;

ring A is substituted by one or more fluorine, chlorine, bromine, $C_1$ to $C_3$-alkyl, hydroxy, $C_1$ to $C_3$-alkyloxy, $C_1$ to $C_3$-alkylthio, amino, $C_1$ to $C_3$-alkylamino, di($C_1$ to $C_3$-alkyl)amino, trifluoromethyl or nitro;

or a pharmaceutically acceptable salt thereof.

Examples of such compounds include:

8-chloro-N,N,4-trimethyl-β,6-diphenyl-4H-[1,2,4]triazolo[4,3-a][1,4]benzodiazepine-1-ethanamine, 8-bromo-N,N,4-trimethyl-β,6-diphenyl-4H-[1,2,4]triazolo[4,3-a][1,4]benzodiazepine-1-ethanamine, 8-fluoro-N,4-dimethyl-β,6-diphenyl-4H-[1,2,4]triazolo[4,3-a][1,4]benzodiazepine-1-ethanamine, 8-methoxy-4-methyl-β,6-diphenyl-4H-[1,2,4]triazolo[4,3-a][1,4]benzodiazepine-1-ethanamine, 8-hydroxy-N,N,4-trimethyl-β,6-diphenyl-4H-[1,2,4]triazolo[4,3-a][1,4]benzodiazepine-1-ethanamine, 8-amino-N,N,4-trimethyl-β,6-diphenyl-4H-[1,2,4]triazolo[4,3-a][1,4]benzodiazepine-1-ethanamine.

This invention also provides novel compounds of the Formula II wherein

R is phenyl;

$R_1$ and $R_2$ are independently hydrogen or $C_1$ to $C_3$-alkyl;

$R_3$ is hydrogen or $C_1$ to $C_3$-alkyl;

$R_4$ is phenyl;

ring A is substituted by one or more iodine groups; or a pharmaceutically acceptable salt thereof.

Examples of such compounds include:

8-iodo-N,N-dimethyl-β,6-diphenyl-4H-[1,2,4]triazolo[4,3-a][1,4]benzodiazepine-1-ethanamine, 8-iodo-N-methyl-β,6-diphenyl4H-[1,2,4]triazolo[4,3-a][1,4]benzodiazepine-1-ethanamine, 8-iodo-β,6-diphenyl-4H-[1,2,4]triazolo[4,3-a][1,4]benzodiazepine-1-ethanamine.

8-iodo-N,N,4-trimethyl-β,6-diphenyl-4H-[1,2,4]triazolo[4,3-a][1,4]benzodiazepine-1-ethanamine, 7,8-diiodo-N,N-dimethyl-β,6-diphenyl-4H-[1,2,4]triazolo[4,3-a][1,4]benzodiazepine-1-ethanamine, 8-iodo-N,4-dimethyl-β,6-diphenyl-4H-[1,2,4]triazolo[4,3-a][1,4]benzodiazepine-1-ethanamine.

The novel compounds of this invention of the Formula II defined hereinabove are prepared by methods known in the art. For example, the method of Hester, Jr., U.S. Pat. No. 4,075,221 is used to prepare the novel compounds of the Formula II wherein $R_1$ and $R_2$ are $C_1$ to $C_3$-alkyl. An appropriate 1-(phenylmethyl)-4H-[1,2,4]triazolo[4,3-a][1,4]benzodiazepine is reacted with a dialkylmethyleneammonium salt prepared either in advance or in situ by reacting an N,N,N',N'-tetraalkyl-diaminomethane and a suitable acylating agent as described in Hester, Jr., U.S. Pat. No. 4,075,221, for example, acetyl chloride, to produce a novel compound of this invention of the Formula II. The requisite starting materials are known in the art or are prepared by methods known in the art.

Compounds of the Formula II wherein one or both of $R_1$ and $R_2$ are hydrogen are prepared as follows. An appropriate N,N-dimethyl-β,6-diphenyl-4H-[1,2,4]triazolo[4,3-a][1,4]benzodiazepine-1-ethanamine is prepared by a method of Hester, Jr., U.S. Pat. No. 4,075,221 or by other known methods and converted to its quaternary ammonium compound by reaction with methyl iodide in a suitable solvent, for example, methanol. The resulting quaternary salt is reacted with ammonia or an appropriate alkylamine at from about 80° to 120° C. for up to 24 hours (in a pressure vessel if required) to produce the desired ethanamine compound of this invention which is isolated and purified by conventional means.

Compounds of the Formulas I or II wherein $R_3$ is $C_1$ to $C_3$-alkyl and compounds of the Formula II wherein R is phenyl substituted by zero to 2 methoxy or ortho-chlorine groups contain asymmetrically substituted carbon atoms and all enantiomers and diastereomers and mixtures thereof of such compounds are included within the scope of this invention.

Examples of acids suitable for making pharmaceutically acceptable acid addition salts of the compounds of Formulas I or II for use according to this invention include such acids as hydrogen chloride, hydrogen bromide, hydrogen iodide, sulfuric acid, orthophosphoric acid, acetic acid, lactic acid, citric acid, succinic acid, benzoic acid, salicyclic acid, pamoic aid, cyclohexanesulfonic acid, methanesulfonic acid, 1- and 2-naphthalene sulfonic acids, p-toluenesulfonic acid, maleic acid, fumaric acid, and the like.

Dosage ranges for use of these compounds can vary from about 0.01 to about 25 mg/kg of the patient's body weight depending upon the compound being used and the extent of fluid loss desired. A general daily dosage range of from about 0.5 to about 2000 mg in single or divided dosage unit forms given two to four times a day for an adult animal is suggested. A single adult human dose ranging from about 0.5 to about 1000 mg can be used depending upon the condition being treated, the age and weight of the patient, the compound being used, and similar factors. Preferred dosages for most applications are 0.5 to 5.0 mg per kg of body weight.

For treating some conditions such as hypokalemia associated with antihypertensive therapy, a physician may desire to prescribe the use of one of these Formula I or II compounds for use in concommitent administration with other diuretics such as hydrochlorothiazide, trichlormethiazide, furosemide, ethoxzolamide, chlorthalidone, and the like, to minimize the loss of potassium from the patient's body. For example, for treating a hypokalemic condition, a physician might want to prescribe for a patient from 0.5 to 2000 mg/day of one of these Formula I or II compounds, or a salt thereof, concommitent with 10 to 200 mg/day of hydrochlorothiazide.

Also, in accordance with this invention, the Formula I or II compounds can be used concommitently with the usual dosages of antihypertensive drugs such as reserpine, deserpidine, hydralazine hydrochloride, mecamylamine hydrochloride, guanadrel sulfate, guanethedine sulfate, methyldopa, pentaerythritol tetranitrate, minoxidil, propranolol, captopril, prazosin, or the like.

The term "dosage unit form" as used in this specification and in the claims refers to physically discrete units suitable as unitary dosages for mammalian subjects, each unit containing as the essential active ingredient a predetermined quantity of a compound of this invention with the required pharmaceutical means which adapt said ingredient for systemic administration. The specification for the novel dosage unit forms of this invention are dictated by and directly dependent on the physical characteristics of the essential active ingredient and the particular effect to be achieved in view of the limitations inherent in the art of compounding such an essential active material for beneficial effects in humans and animals, these being features of the present invention. Examples of suitable dosage unit forms in accordance with this invention are tablets, capsules, orally administered liquid preparations in suitable liquid vehicles, sterile preparations in suitable liquid vehicles for intramuscular and intravenous administration, suppositories, and sterile dry preparations for the extemporaneous preparation of sterile injectable preparations in a suitable liquid vehicle. Suitable solid diluents or carriers for the solid oral pharmaceutical dosage unit forms are selected from the group consisting of lipids, carbohydrates, proteins and mineral solids, for example, starch, surcrose, lactose, kaolin, dicalcium phosphate, gelatin, acacia, corn syrup, corn starch, talc and the like. Capsules, both hard and soft, are filled with compositions of these ethanamine active ingredients in combination with suitable diluents and excipients, for example, edible oils, talc, calcium carbonate and the like and also calcium stearate. Liquid preparations for oral administration are prepared in water or aqueous vehicles which advantageously contain suspending agents, for example, methylcellulose, acacia, polyvinylpyrrolidone, polyvinyl alcohol and the like. In the case of injectable forms, the injectable formulation must be sterile and must be fluid to the extent that easy syringeability exists. Such preparations must be stable under the conditions of manufacture and storage, and ordinarily contain in addition to the basic solvent or suspending liquid, preservatives in the nature of bacteriostatic and fungistatic agents, for example, parabens, chlorobutanol, benzyl alcohol, phenol, thimerosal, and the like. In many cases, it is preferable to include osmotically active agents, for example, sugars or sodium chloride in isotonic concentrations. Carriers and vehicles include vegetable oils, ethanol, polyols, for example glycerol, propylene glycol, liquid polyethylene glycol, and the like. Any solid preparations for subsequent extemporaneous preparation of sterile injectable preparations are sterilized, preferably by exposure to a sterilizing gas, for example, ethylene oxide. The aforesaid carriers, vehicles, diluents, excipients, preservatives, isotonic agents and the like constitute the pharmaceutical means which adapt the preparations for systemic administration.

The pharmaceutical dosage unit forms are prepared in accordance with the preceding general description to provide from about 0.5 to about 1000 mg of the essential active ingredient per dosage unit form, which as aforesaid may be in the form of a semi-solid or solid, topical, oral or rectal preparation, a liquid oral preparation, an injectable preparation including liquid preparations and solid dry preparations for extemporaneous reconstitution to a liquid injectable preparation. The amount of the essential active ingredient provided in the pharmaceutical dosage unit forms is that amount sufficient to obtain diuretic effects often accompanied by antihypertensive effects within the aforesaid effective non-toxic range.

The useful pharmaceutical dosage unit forms of these compounds in pharmaceutical formulations are preferably adapted for systemic administration to obtain diuretic effects comprising an effective, nontoxic amount of a compound according to Formula I or II or as its pharmacologically acceptable salt.

Examples of compounds of Formula I or II which can be used in the practice of this invention include:
8-chloro-N,N-dimethyl-$\beta$,6-diphenyl-4H-[1,2,4]triazolo[4,3-a][1,4]benzodiazepine-1-ethanamine,
8-bromo-N,N-dimethyl-6-phenyl-4H-[1,2,4]triazolo[4,3-a][1,4]benzodiazepine-1-ethanamine,
8-bromo-N,N-dimethyl-$\beta$,6-diphenyl-4H-[1,2,4]triazolo[4,3-a][1,4]benzodiazepine-1-ethanamine,
8-chloro-$\beta$,6-diphenyl-4H-[1,2,4]triazolo[4,3-a][1,4]benzodiazepine-1-ethanamine,
N,N-dimethyl-8-(methylthio)-$\beta$,6-diphenyl-4H-[1,2,4]triazolo[4,3-a][1,4]benzodiazepine-1-ethanamine,
8-chloro-$\beta$-(3-methoxyphenyl)-N,N-dimethyl-6-phenyl-4H-[1,2,4]triazolo[4,3-a][1,4]benzodiazepine-1-ethanamine,
8-chloro-$\beta$-(2-chlorophenyl)-N,N-dimethyl-6-phenyl-4H-[1,2,4]triazolo[4,3-a][1,4]benzodiazepine-1-ethanamine,
8-chloro-N,N,4-trimethyl-$\beta$,6-diphenyl-4H-[1,2,4]triazolo[4,3-a][1,4]benzodiazepine-1-ethanamine,
8-chloro-N,N-dimethyl-$\beta$-(4-methoxyphenyl)-6-phenyl-4H-[1,2,4]triazolo[4,3-a][1,4]benzodiazepine-1-ethanamine,
8-iodo-N,N-dimethyl-$\beta$,6-diphenyl-4H-[1,2,4]triazolo[4,3-a][1,4]benzodiazepine-1-ethanamine,
8-chloro-N,N-dimethyl-$\beta$-(2-methoxyphenyl)-6-phenyl-4H-[1,2,4]triazolo[4,3-a][1,4]benzodiazepine-1-ethanamine,
8-bromo-N,N-dimethyl-6-(2-pyridinyl)-4H-[1,2,4]triazolo[4,3-a][1,4]benzodiazepine-1-ethanamine, and the like, or a pharmaceutically acceptable salt thereof.

Compounds of the Formula I, wherein $R_4$ is phenyl, and methods to prepare them, are disclosed in Hester, Jr., U.S. Pat. No. 3,759,943, and the method of treating depression with such compounds is disclosed in Hester, Jr., U.S. Pat. No. 3,969,504. Compounds of the Formula I, wherein $R_4$ is pyridinyl, and methods to prepare them, are disclosed in Hester, Jr., U.S. Pat. No. 3,767,661. Some of the Formula II compounds herein are known from Hester, Jr., U.S. Pat. No. 4,075,221 and are prepared by a method described therein.

Of these various compounds a lead compound with regard to diuretic properties is 8-chloro-N,N-dimethyl-$\beta$,6-diphenyl-4H-[1,2,4]triazolo[4,3-a][1,4]benzodiazepine-1-ethanamine.

The diuretic property of the Formula I or II compounds was determined by way of the following standard laboratory animal test.

TEST PROCEDURE AND RESULTS OF TEST FOR REPRESENTATIVE COMPOUNDS

The following standard laboratory animal test for diuretic activity of test chemical compounds, compared against untreated control test animals as well as against animals treated with commercially available standard diuretic drug compounds was used to test compounds included within the scope of this invention.

PROCEDURE FOR DIURETIC SCREEN IN RATS WITH ORAL ADMINISTRATION OF TEST COMPOUNDS

Procedure of Test

Male TUC/SD (The Upjohn Company/Sprague Dawley) rats weighing approximately 160 g are used for the diuretic screen. The rats are deprived of food 24 hours prior to test time but have access to water ad lib. until 1½ hours before test time. From that point on and throughout the test period both food and water are withheld. Tests are conducted in a temperature (75° F.) and humidity (48%) controlled laboratory.

Tests are initiated by simultaneous hydration and oral administration of test agents. This is accomplished by gavage with 25 ml/kg of normal saline (0.9%) containing carboxymethylcellulose (0.5%) and the test compounds (either dissolved or suspended). The rats are placed in metabolism cages (2 rats/cage) and urine collected over the ensuing 5 hours. Rats in 10 cages serve as controls, those in 2 cages receive hydrochlorothiazide (40 mg/kg) as the test standard and rats in the remaining cages (usually 44) receive test compounds. Each test compound is given orally to 4 rats (2 cages) at a dose of 40 mg/kg.

Analysis of Test Results

Criteria for declaring test compounds "active" or "inactive" were established as described by Roseberry and Gehan[1]. Accordingly, testing is conducted in two stages:

Stage 1—A ratio, denoted $(T/C)_1$, of the mean urine volume of treated (test compound) and control rats is determined for each test compound. If $(T/C)_1$ is <1.66, the test compound is declared "inactive." If $(T/C)_1$ is 1.66 or greater, the test compound is retested in Stage 2.

Stage 2—A ratio, denoted $(T/C)_2$, of the mean urine volume of treated and control rats is determined for each retested compound and the product of the two ratios is calculated. If $(T/C)_1 \cdot (T/C)_2$ is <3.34, the retested compound is declared "inactive". If this product is 3.34 or greater, the compound is declared "active".

[1] T. D. Roseberry and E. A. Gehan. Operating Characteristic Curves and Accept-Reject Rules for Two and Three Stage Screening Procedures. Biometrics 20:73–84, 1964.

The respective decision values for Stages 1 and 2 are determined from cumulative data obtained in control and hydrochlorothiazide (test standard) treated rats. These are subject to periodic reevaluation. With this two-stage procedure, the expected probability of a test compound with a true T/C of 2.25 being accepted is 0.99 while the probability of a test compound with a true T/C of 1.5 being accepted is less than 0.01.

The following compounds were tested in the above test procedure to give the data in the table which follows:

| Compound | Name |
|---|---|
| 1 | 8-Chloro-N,N—dimethyl-β,6-diphenyl-4H—[1,2,4]triazolo[4,3-a][1,4]benzodiazepine-1-ethanamine |
| 2 | 8-Bromo-N,N—dimethyl-6-phenyl-4H—[1,2,4]triazolo[4,3-a][1,4]benzodiazepine-1-ethanamine, p-toluenesulfonate |
| 3 | 8-Bromo-N,N—dimethyl-β,6-diphenyl-4H—[1,2,4]triazolo[4,3-a][1,4]benzodiazepine-1-ethanamine |
| 4 | 8-Chloro-β,6-diphenyl-4H—[1,2,4]triazolo[4,3-a][1,4]benzodiazepine-1-ethanamine, monohydroiodide |
| 5 | N,N—dimethyl-8-(methylthio)-β,6-diphenyl-4H—[1,2,4]triazolo[4,3-a][1,4]benzodiazepine-1-ethanamine |
| 6 | 8-Chloro-β-(3-methoxyphenyl)-N,N—dimethyl-6-phenyl-4H—[1,2,4]triazolo[4,3-a][1,4]-benzodiazepine-1-ethanamine |
| 7 | 8-Chloro-β-(2-chlorophenyl)-N,N—dimethyl-6-phenyl-4H—[1,2,4]-triazolo[4,3-a][1,4]-benzodiazepine-1-ethanamine |
| 8 | 8-Chloro-N,N,4-trimethyl-β,6-diphenyl-4H—[1,2,4]triazolo[4,3-a][1.4]benzodiazepine-1-ethanamine |
| 9 | 8-Chloro-β-(4-methoxyphenyl)-N,N—dimethyl-6-phenyl-4H—[1,2,4]triazolo[4,3-a][1,4]-benzodiazepine-1-ethanamine |
| 10 | 8-Iodo-N,N—dimethyl-β,6-diphenyl-4H—[1,2,4]triazolo[4,3-a][1,4]benzodiazepine-1-ethanamine |
| 11 | 8-Chloro-β-(2-methoxyphenyl)-N,N—dimethyl-6-phenyl-4H—[1,2,4]triazolo[4,3-a][1,4]-benzodiazepine-1-ethanamine |
| 12 | 8-Bromo-N,N—dimethyl-6-(2-pyridinyl)-4H—[1,2,4]triazolo[4,3-a][1,4]benzodiazepine-1-ethanamine |

In the above described tests these twelve (12) compounds were rated "active" as diuretic drugs, based upon the following data:

| Compound No. | Urine Volume Ratios | | T/C₁XT/C₂ Value |
|---|---|---|---|
| | T/C₁ | T/C₂ | |
| 1 | 2.51 | 2.10 | 5.27 |
| 2 | 2.63 | 2.98 | 7.84 |
| 3 | 2.18 | 2.17 | 4.73 |
| 4 | 2.34 | 2.53 | 5.92 |
| 5 | 2.88 | 2.29 | 6.60 |
| 6 | 2.3 | 3.18 | 7.31 |
| 7 | 2.26 | 1.67 | 3.77 |
| 8 | 2.31 | 3.05 | 7.05 |
| 9 | 2.77 | 2.00 | 5.57 |
| 10 | 3.26 | 2.88 | 9.44 |
| 11 | 2.69 | 1.87 | 5.03 |
| 12 | 1.75 | 1.98 | 3.47 |

These diuretic activity findings for this type of triazolobenzodiazepine compounds are believed to be surprising and unexpected because some other closely related compounds either did not pass the first of the two above-described urine volume tests, or did not get a high enough rating in the second urine volume test so that the multiplier value (3rd column value) was high enough to rate the compound as "active" in this standard laboratory animal diuretic test. Compounds which were rated inactive in these diuretic tests include:

| (A) | 8-chloro-1-[2-(diethylamino)ethyl]-6-phenyl-4H—[1,2,4]triazolo[4,3-a][1.4]benzodiazepine |
|---|---|
| (B) | 8-chloro-1-(2-aminoethyl)-6-phenyl-4H—[1,2,4]triazolo[4,3-a][1,4]benzodiazepine |
| (C) | 1-[2-(N,N—dimethylamino)ethyl]-6-phenyl-4H—[1,2,4]triazolo[4,3-a][1,4]benzodiazepine |
| (D) | 1-(2-aminoethyl)-6-phenyl-4H—[1,2,4]triazolo-[4,3-a][1,4]benzodiazepine |
| (E) | 1-[2-(N,N—dimethylamino)ethyl]-6-(2-chlorophenyl)-4H—[1,2,4]triazolo[4,3-a][1,4]benzodiazepine |
| (F) | 8-bromo-1-(2-aminoethyl)-6-phenyl-4H—[1,2,4]-triazolo[4,3-a][1,4]benzodiazepine |
| (G) | N,N—dimethyl-β,6-diphenyl-4H—[1,2,4]triazolo-[4,3-a][1,4]benzodiazepine-1-ethanamine |
| (H) | 8-chloro-N,N—dimethyl-β-phenyl-6-(2-chlorophenyl)-4H—[1,2,4]triazolo[4,3-a][1,4]benzodiazepine-1-ethanamine |

In this specification and in the detailed examples which follow the following abbreviations have the indicated meaning. $N_2$ means nitrogen gas; DMF means N,N-dimethylformamide; mmole means millimole; $NaHCO_3$ means sodium bicarbonate; $CH_2Cl_2$ means methylene chloride; $Na_2SO_4$ means anhydrous sodium sulfate; THF means tetrahydrofuran; $H_2O$ means water; NaCl means sodium chloride; brine means a saturated aqueous NaCl solution; EtOAc means ethyl acetate; Skelly B (or Skellysolve B) is a tradename for a solvent of essentially n-hexane, bp 60°–68° C. (Merck Index, Ninth Edition (1976) page 1106); hr means hour or hours; min means minutes; MeOH means absolute methanol; EtOH means absolute ethanol; IR means infra-red spectrum and analysis; UV means ultraviolet spectrum and analysis; NMR means nuclear magnetic resonance spectrum and analysis; MS means mass spectrum and analysis; Anal means analysis; $P_2S_5$ means phosphorous pentasulfide; HCl means hydrogen chloride; $Et_2O$ means diethyl ether; pet. ether means light petroleum ether of bp about 35°–37° C.; NaOH means sodium hydroxide; TLC means thin layer chromatography procedures; butanol generally means n-butanol.

EXAMPLE 1

8-Chloro-β,6-diphenyl-4H-[1,2,4]triazolo[4,3-a][1,4]benzodiazepine-1-ethanamine, and its monohydriodide salt A. Quaternary Salt Preparation—2-(8-Chloro-6-phenyl-4H-[1,2,4]triazolo[4,3-a][1,4]benzodiazepin-1-yl)-N,N,N-trimethyl-2-phenylethanaminium iodide To an ice-cooled, nitrogen gas covered solution of 10.0 g (22.6 mmol) of 8-chloro-N,N-dimethyl-β,6-diphenyl-4H-[1,2,4]triazolo[4,3-a][1,4]benzodiazepine-1-ethanamine (See Example 10 of U.S. Pat. No. 4,075,221) in 175 ml of methanol, there was added 16.90 ml (38.54 g, 0.272 mol) of methyl iodide over 18 minutes. The solution was stirred at room temperature for 6.5 hours during which time a solid crystallized. The suspended solid was collected on a filter, washed with a small amount of methanol and dried to yield 9.82 g (68.1% yield) of the titled quaternary ammonium iodide salt, m.p. 216°–217° C. (dec.), containing some methanol solvation. The filtrate from the filtration step was combined and concentrated in vacuo to obtain a crude solid residue, which residue was recrystallized from methanol to yield 3.28 g (22.7%) of the subtitled quaternary ammonium iodide salt, m.p. 214°–215° C. (dec.) and 0.48 g (3.3% yield) of another crop of the subtitled quaternary ammonium iodide salt, m.p. 212°–214° C. (dec.). An analytical sample of this material was recrystallized from methanol to give the subtitled quaternary ammonium iodide salt, m.p. 217°–218° C., which analyzed as follows:

Anal. Calcd. for $C_{27}H_{27}N_5ClI$: C, 55.55; H, 4.66; N, 12.00%. Found (anal. corrected for 9.03% MeOH): C, 56.13; H, 4.34; N, 12.54%.

B. 8-Chloro-$\beta$,6-diphenyl-4H-[1,2,4]triazolo[4,3-a][1,4]benzodiazepine-1-ethanamine, characterized as its monohydriodide salt A mixture of 4.0 g (6.85 mmol) of the quaternary ammonium salt from Part A above and 200 ml of freshly distilled ammonia was sealed in a pressure reaction vessel and heated in an oil bath at 100° C. under 650 psig for 18 hours and then allowed to cool. The reaction mixture was removed from the pressure vessel and concentrated under a stream of nitrogen. The residue was treated with 400 ml of a 1:1 v/v mixture of ethyl acetate and methylene dichloride. A solid (A) which was suspended in the mixture was collected on a filter and the filtrate was concentrated to ⅓ of its volume. An additional solid (B) came out of this concentrated filtrate and was similarly separated by filtration. Solid (B) was suspended and crystallized from acetonitrile to yield 0.50 g (13.5% yield) of the tilted amine as its hydriodide, m.p. 257°–259° C. and 0.11 g (3.0% yield) of the same amine hydriodide salt, m.p. 265.5°–267° C. solvated with acetonitrile.

Solid A was also crystallized from acetonitrile to yield 1.10 g (29.6% yield) of the titled amine as its hydriodide, m.p. 270°–273° C. and 0.18 g (4.8% yield) of the same amine hydriodide salt, m.p. 270°–273° C. free of acetonitrile.

Anal. Calcd. for $C_{24}H_{20}N_5Cl \cdot HI$: C, 53.20; H, 3.90; N, 12.93; Cl, 6.55%. Found: C, 53.01; H, 3.88; N, 13.24; Cl, 6.54%.

This amine salt can be converted, if desired, to its tilted free amine form by treating the amine hydriodide salt with aqueous sodium bicarbonate solution, according to known chemical procedures.

EXAMPLE 2

General procedure for the preparation of $\beta$,6-diaryl-4H-[1,2,4]triazolo[4,3-a][1,4]benzodiazepine-1-ethanamines of the Formula II wherein $R_1$ and $R_2$ are $C_1$ to $C_3$-alkyl To an ice cooled $N_2$ covered mixture of 2.0 mmole of the 1-(phenylmethyl)triazolobenzodiazepine, 2.2 mmole of N,N,N',N'-tetraalkyldiaminomethane in 15 ml of DMF was added 2.3 mmole of acetyl chloride dropwise. The reaction was stirred for from 3–5 hours at about 0° to 10° C. If not complete an additional 0.1–0.5 mmole of acetyl chloride was added and stirring was continued for up to a total of 24 hours. When complete the reaction was poured into a mixture of ice:aqueous $NaHCO_3$. The mixture was extracted with $CH_2Cl_2$ and the organic layer was washed with dilute brine, dried over $Na_2SO_4$ and concentrated in vacuo. Chromatography of the residue over silica gel eluting with methanol and/or recrystallization from ethyl acetate or from diethyl ether-light petroleum ether (bp 35°–37° C.) yielded the product.

EXAMPLE 3

8-Chloro-$\beta$-(4-methoxyphenyl)-N,N-dimethyl-6-phenyl-4H-[1,2,4]triazolo[4,3-a][1,4]benzodiazepine-1-ethanamine A. General procedure for the preparation of 1-(Phenylmethyl) intermediates as exemplified by the preparation of 8-chloro-1-(4-methoxyphenylmethyl)-6-phenyl-4H-[1,2,4]triazolo[4,3-a][1,4]benzodiazepine A mechanically stirred solution of 4-methoxyphenylacetic acid (1.66 g, 0.01 mole) in THF (30 ml), under $N_2$, was cooled in an ice bath and treated with carbonyl diimidazole (CDI). After 1 hour 7-chloro-2-hydrazino-5-phenyl-3H-1,4-benzodiazepine (2.56 g, 0.009 mole) was added and the reaction was allowed to continue until a precipitate began to form (usually in approximately 4–6 hours), at which time the ice bath was removed and the reaction allowed to stir at ambient temperature for 16 hours. The precipitate was filtered, washed with THF and dried in the vacuo oven overnight. In experiments where this precipitate appeared to be slightly soluble in THF, the filtrate was concentrated in vacuo and the residue mixed with $CH_2Cl_2$ and $H_2O$. The $CH_2Cl_2$ solution was washed with brine, dried over $Na_2SO_4$ and concentrated in vacuo to yield additional product.

A stirred mixture of the above product in aetic acid (50 ml) was refluxed, under $N_2$, for 2–3 hours then concentrated in vacuo. The residue was mixed with $CH_2Cl_2$ and $H_2O$. The $Ch_2Cl_2$ was washed with aqueous $NaHCO_3$ and brine, dried over $Na_2SO_4$ and concentrated in vacuo. This material was crystallized from EtOAc-Skelly B to give a 54.8% yield of the subtitled intermediate, mp 183° C. The analytical sample had a C:H:N:Cl ratio of 69.60:4.68: 13.73:8.62. Calculated for $C_{24}H_{19}N_4ClO$: 69.47:4.62:13.50:8.55.

B. 8-Chloro-N,N-dimethyl-$\beta$-(4-methoxyphenyl)-6-phenyl-4H-[1,2,4]triazolo[4,3-a][1,4]benzodiazepine-1-ethanamine A stirred solution of the compound from Part A above (2.0 g, 0.005 ml) in DMF (25 ml) was cooled in an ice bath, treated with N,N,N',N'-tetramethyldiaminomethane (0.819 ml, 0.006 mol) and then dropwise with acetyl chloride (0.5 ml, 0.00704 mol). The mixture was kept in the ice bath for 5 hours 15 minutes and poured into a mixture of ice and saturated $NaHCO_3$. The mixture was extracted with $CH_2Cl_2$; the extract was washed with dilute NaCl, dried ($Na_2SO_4$) and concentrated in vacuo using xylene to help remove last traces of DMF. The residue was chromatographed on silica gel with MeOH. The product thus obtained was crystallized from EtOAc-Skelly B to give: 1.38 g, mp 138.5°–145° and 0.26 g, mp 137.5°–142.5° of the titled product. The analytical sample had mp 136°–142°. The structure was supported by IR, UV, NMR and MS.

Anal. calcd. for $C_{27}H_{26}ClN_5O$: C, 68.71; H, 5.55; Cl, 7.51; N, 14.84. Found: C, 68.41; H, 5.79; Cl, 7.45; N, 14.68; $H_2O$, 0.64.

EXAMPLE 4

8-Chloro-β-(3-methoxyphenyl)-N,N-dimethyl-6-phenyl-4H-[1,2,4]triazolo[4,3-a][1,4]benzodiazepine-1-ethanamine A. 8-Chloro-1-(3-methoxyphenylmethyl)-6-phenyl-4H-[1,2,4]triazolo[4,3-a][1,4]benzodiazepine A mechanically stirred solution of 3-methoxyphenylacetic acid (1.66 g, 0.01 mol) in THF (30 ml), under $N_2$, was cooled in an ice bath and treated with carbonyl diimidazole (CDI). After one hour 7-chloro-2-hydrazino-5-phenyl-3H-1,4-benzodiazepine (2.56 g, 0.009 mol) was added and the reaction was allowed to continue until a precipitate began to form (usually in approximately 4–6 hours), at which time the ice bath was removed and the reaction allowed to stir at ambient temperature for 16 hours. The precipitate was filtered, washed with THF and dried in the vacuum oven overnight. In experiments where this precipitate appeared to be slightly soluble in THF, the filtrate was concentrated in vacuo and the residue mixed with $CH_2Cl_2$ and $H_2O$. The $CH_2Cl_2$ solution was washed with brine, dried over $Na_2SO_4$ and concentrated in vacuo to yield additional product.

A stirred mixture of the above product in acetic acid (50 ml) was refluxed, under $N_2$, for 2-3 hours then concentrated in vacuo. The residue was mixed with $Ch_2Cl_2$ and $H_2O$. The $CH_2Cl_2$ was washed with aqueous $NaHCO_3$ and brine, dried over $Na_2SO_4$ and concentrated in vacuo. This material was crystallized from EtOAc-Skelly B to give 1.08 g, mp 133°-134° and 0.56 g, mp 135°-137° of the subtitled intermediate. The analytical sample had mp 132°-135° and a C:H:N:Cl ratio of 69.09:4.60:13.52:8.52. Calculated for $C_{24}H_{19}N_4ClO$: 69.47:4.62:13.50:8.55.

B. 8-Chloro-β-(3-methoxyphenyl)-N,N-dimethyl-6-phenyl-4H-[1,2,4]triazolo[4,3-a][1,4]benzodiazepine-1ethanamine To an ice cooled $N_2$ covered mixture of 2.0 mmole of the compound from Part A above, 2.2 mmole of N,N,N',N'-tetramethyldiaminomethane in 15 ml of DMF was added 2.3 mmole of acetyl chloride dropwise. The reaction was stirred for from 3-5 hours at 4° C. An additional 0.1-0.5 mmole of acetyl chloride was added and stirring was continued for a total of 16 hours. When complete the reaction was poured into a mixture of ice:aqueous $NaHCO_3$. The mixture was extracted with $Ch_2Cl_2$ and the organic layer was washed with dilute brine, dried over $Na_2SO_4$ and concentrated in vacuo. Chromatography of the residue over silica gel eluting with methanol and recrystallization from diethyl ether-petroleum ether yielded the titled product, mp 139°-140°, which had a C:H:N:Cl ratio of 68.30:5.76:14.79:7.63. Calculated for $C_{27}H_{26}ClN_5O$: 68.71:5.55:14.84:7.51.

EXAMPLE 5

8-Chloro-N,N-4-trimethyl-β,6-diphenyl-4H-[1,2,4]triazolo[4,3-a][1,4]benzodiazepine-1-ethanamine A. 7-Chloro-1,3-dihydro-3-methyl-5-phenyl-2H-1,4-benzodiazepine-2-thione A stirred mixture of 7-chloro-1,3-dihydro-3-methyl-5-phenyl-2H-1,4-benzodiazepin-2-one (10 g, 0.035 mol) in pyridine (300 ml), treated with $P_2S_5$ (8.0 g, 0.036 mmol) was refluxed, under $N_2$, for 2 hours then concentrated in vacuo. To remove the remaining pyridine the residue was combined with toluene twice with concentration after each addition. The remaining material was mixed with cold $NaHCO_3$ and extracted twice with $CH_2Cl_2$. At this point a precipitate thought to be undissolved product formed between the two layers. This was filtered and washed with $CH_2Cl_2$ and $H_2O$. The $NaHCO_3$ layer was extracted with $CH_2Cl_2$ again. The combined $CH_2Cl_2$ extracts were washed with brine, dried over $Na_2SO_4$, and concentrated in vacuo. The residue was crystallized from EtOAc-Skelly B to give 3.0 g of the subtitled intermediate, mp 250°. The precipitate was also recrystallized from EtOAc-Skelly B to give 3.01 g of additional subtitled intermediate, mp 255°.

B. 8-Chloro-4-methyl-1-phenylmethyl-4H-[1,2,4]triazolo[4,3-a][1,4]benzodiazepine A stirred mixture of 7-chloro-1,3-dihydro-3-methyl-5-phenyl-2H-1,4-benzodiazepine-2-thione (3.0 g, 0.01 mol), phenyl acetic acid hydrazide (4.95 g, 0.033 mol) and butanol (150 ml) was refluxed for 16 hours while $N_2$ was being bubbled through the mixture. The reaction mixture was concentrated under high vacuum, and the residue mixed with iced $H_2O$. The product was filtered and dissolved in $CH_2Cl_2$. The $CH_2Cl_2$ was washed with dilute HCl and brine, dried over $Na_2SO_4$ and concentrated in vacuo. At this point it appeared that complete cyclization had not been achieved. Therefore, the residue was combined with acetic acid (100 ml) and refluxed for 2 hours under $N_2$. The reaction mixture was concentrated in vacuo and the residue mixed with $CH_2Cl_2$ and $H_2O$. The $CH_2Cl_2$ was washed with $NaHCO_3$ and brine, dried over $Na_2SO_4$ and concentrated in vacuo. The material was crystallized from EtOAc-Skelly B to give 1.55 g, mp 195°-197° of the subtitled intermediate, which had a C:H:N:Cl ratio of 72.38:4.85:14.16:8.81. Calculated for $C_{24}H_{19}N_4Cl$: 72.26:4.80:14.05:8.89.

C. 8-Chloro-N,N,4-trimethyl-β,6-diphenyl-4H-[1,2,4]triazolo[4,3-a][1,4]benzodiazepine-1-ethanamine A stirred solution of the compound from Part B above (3.0 g, 0.0075 mol) in DMF (80 ml) was cooled in an ice bath under $N_2$ and treated with N,N,N',N'-tetramethyldiaminomethane (1.32 ml, 0.0097 mol) and then dropwise with acetyl chloride (0.74 ml, 0.0104 mol). The mixture was kept in the ice bath for 18 hours and poured into a mixture of ice and saturated $NaHCO_3$. This mixture was extracted with $CH_2Cl_2$. The extract was washed with brine, dried ($Na_2SO_4$) and concentrated in vacuo using xylene to help remove residual DMF. The residue was crystallized from $Et_2O$-petroleum ether to give 2.4 g of the titled compound, mp 200°-103°. The analytical sample was recrystallized from EtOAc and had mp 204°-205°. The structure was supported by IR, UV, NMR and MS.

Anal. calcd. for $C_{27}H_{26}ClN_5$: C, 71.11; H, 5.75; Cl, 7.78; N, 15.36. Found: C, 70.78; H, 5.79; Cl, 7.79; N, 15.27.

EXAMPLE 6

8-Iodo-N,N-dimethyl-β, 6-diphenyl-4H-[1,2,4]triazolo[4,3-a][1,4benzodiazepine-1-ethanamine A. 1,3-Dihydro-7-iodo-5-phenyl-2H-1,4-benzodiazepin-2-one Bromoacetyl bromide (50.06 g, 0.248 mol) was added dropwise to a stirred solution of 2-amino-5-iodobenzophenone (40.0 g, 0.124 mol) in toluene (800 ml), under $N_2$. After the addition was complete the reaction mixture was heated to 800° C. for 4 hours. The mixture was allowed to cool to ambient temperature and then treated with 20% NaOH (500 ml); it was stirred for 15 minutes and the layers were separated. The aqueous layer was extracted with CH$_2$Cl$_2$. The organic layers were combined, washed with brine, dried (Na$_2$SO$_4$) and concentrated in vacuo. The residue was crystallized from MeOH to yield 38.22 g (69.42%), mp 124°–125° and 9.66 g (17.54%), mp 125°–126° of the α-bromoacetamide intermediate.

Ammonia (2150 ml) was condensed into a flask fitted with a cold finger condenser, and a mechanical stirrer with the reaction vessel immersed in a dry ice acetone bath. The α-bromoacetamide (40 g, 0.09 mol) obtained above was then added and the dry ice bath removed allowing the reaction mixture to reflux. After 2 hours the ammonia was allowed to evaporate under a slow stream of N$_2$. The residue was combined with CH$_2$Cl$_2$ (450 ml) and H$_2$O (250 ml) and stirred for 15 minutes. The layers were separated and the aqueous layer was extracted with CH$_2$Cl$_2$. The combined organic extracts were dried (Na$_2$SO$_4$) and concentrated. The resulting residue was combined with EtOH (500 ml) and heated to reflux with portions of EtOH being distilled off and replaced with fresh EtOH periodically during the reaction. After 2½ hours the reaction mixture was decolorized, partially concentrated in vacuo and allowed to crystallize yielding 20.67 g (63.4%) of the subtitled intermediate, mp 223°–225°. Further concentration yielded an additional 5.64 g (17.3%) mp 220°–222° of the subtitled intermediate. The product was one spot by TLC (2% MeOH:CH$_2$Cl$_2$). The analytical sample was recrystallized from EtOH and had mp 223°–225°. The structure was supported by IR, UV, NMR, and MS.

Analysis Calc'd for C$_{13}$H$_{11}$IN$_2$O: C, 49.74; H, 3.06; I, 35.04; N, 7.74. Found: C, 50.14; H, 3.31; I, 34.86; N, 7.76.

B. 1,3-Dihydro-7-iodo-5-phenyl-2H-1,4-benzodiazepine-2-thione

A stirred mixture of phosphorus pentasulfide (1.2 g, 0.0054 mol) and pyridine (50 ml) was placed in a preheated oil bath (130° C.), under N$_2$. After the phosphorus pentasulfide had dissolved, the amide from Part A above (2.0 g, 0.0055 mol) was added and the mixture quickly heated to reflux. After refluxing 45 minutes the reaction mixture was cooled in an ice bath and concentrated in vacuo. The residue was combined with a small amount of CH$_2$Cl$_2$ and ice cold aqueous NaHCO$_3$ (50 ml) and stirred in an ice bath for 45 minutes. The resulting suspension was filtered and the solid was washed with CH$_2$Cl$_2$ and H$_2$O and dried in vacuo to yield 1.53 g of the subtitled intermediate, mp 248°–250°. This product was found to be one spot on TLC (2% MeOH:CH$_2$Cl$_2$). The structure was supported by NMR. In an attempt to retrieve more product the filtrate was separated into its respective layers and the aqueous layer extracted with CH$_2$Cl$_2$. The pooled organic extracts were washed with brine, dried (Na$_2$SO$_4$) and concentrated in vacuo. The residue was suspended in a small amount of CH$_2$Cl$_2$ and filtered to yield 0.20 g, mp 237°–238°, which was found to be impure product by TLC.

In subsequent runs it was found that the P$_2$S$_5$ complex generated in this reaction was difficult to decompose. Useful product was obtained by stirring the crude product with saturated NaHCO$_3$ and a large volume of CH$_2$Cl$_2$. When the solid had dissolved the CH$_2$Cl$_2$ solution was washed (dilute NaCl), dried (Na$_2$SO$_4$), concentrated to a small volume, diluted with EtOH and crystallized to give the subtitled intermediate, mp 238.5°–239.5° (dec.).

C. 8-Iodo-6-phenyl-1-(phenylmethyl)-4H-[1,2,4]triazolo[4,3-a][1,4]benzodiazepine A stirred mixture of 7-iodo-1,3-dihydro-5-phenyl-2H-1,4-benzodiazepine-2-thione (3.78 g, 0.01 mol), phenylacetic acid hydrazide (4.5 g, 0.03 mol) and butanol (150 ml) was heated to reflux while N$_2$ was bubbled through the mixture. After refluxing 17 hours the reaction mixture was concentrated under vacuum. The residue was combined with ice water and allowed to stir for a few minutes. The resulting suspension was filtered and the filtered material washed with CH$_2$Cl$_2$. The filtrate was separated into its respective layers and the aqueous layer washed with CH$_2$Cl$_2$. The combined organic fractions were washed with brine, dried (Na$_2$SO$_4$) and concentrated in vacuo. The residue was triturated with EtOAc to yield 1.43 g (30.04%), mp 200°–201° of the subtitled intermediate. The analytical sample was recrystallized from EtOAc and had mp 201°–202°. The IR, NMR and mass spectra supported the proposed structure.

Anal. Calc'd for C$_{23}$H$_{17}$N$_4$I: C, 58.00; H, 3.60; N, 11.76; I, 26.64. Found: C, 57.74; H, 3.55; N, 11.64; I, 26.39.

D. 8-Iodo-N,N-dimethyl-β,6-diphenyl-4H-[1,2,4]triazolo[4,3-a][1,4]benzodiazepine-1-ethanamine A stirred solution of the compound from Part C above (0.953 g, 0.002 mol) in DMF (14 ml) was cooled, under N$_2$, in an ice bath and treated with N,N,N',N'-tetramethyldiaminomethane (0.328 ml, 0.0024 mol) and then dropwise with acetyl chloride (0.2 ml, 0.0028 mol). A light precipitate formed that became heavier as the reaction progressed. The mixture was kept in the ice bath for 8 hours 10 minutes and then poured into a mixture of ice and saturated NaHCO$_3$. This was extracted with CH$_2$Cl$_2$. The extract was washed with dilute NaCl, dried (Na$_2$SO$_4$) and concentrated in vacuo using xylene to help remove residual DMF. The residue was chromatographed on silica gel with MeOH. The pure product thus obtained was crystallized from Et$_2$O-petroleum ether to give 0.284 g, mp 192.5°–193.5°, and 0.033 g, mp 192°–193°, of the title product. Early fractions from this column contained a mixture of recovered starting material and product. This was rechromatographed on silica gel with 10% MeOH-CHCl$_3$. The product obtained from this column was crystallized from EtOAc-Skelly B to give 0.248 g, mp 194°–195.5°, and 0.064 g, mp 192.5°–194° of additional titled product. The analytical sample was recrystallized from EtOAc-Skelly B and had mp 194°–196°. The structure was supported by IR, UV, NMR, and MS.

Anal. Calc'd for C$_{26}$H$_{24}$N$_5$I: C, 58.55; H 4.53; I, 23.79; N, 13.13. Found: C, 58.17; H, 4.50; I, 22.75, 24.03; N, 13.39.

EXAMPLE 7

General procedure for the preparation of β,6-Diaryl-4H-[1,2,4]triazolo[4,3-a][1,4]benzodiazepine-1-ethanamines of the Formula II wherein one or both of R$_1$ and R$_2$ are hydrogen A mixture of 3.5 mmole of the amine quaternary salt and an excess of the appropriate amine was reacted under N$_2$ in an oil bath at about 80° to 120° C. for up to 24 hours and allowed to cool.

Work-up 1: The reaction mixture was poured into ice:saturated aqueous NaHCO$_3$. If crystalline the solid was filtered, if not the mixture was extracted with CH₂Cl₂ and the extract was washed with dilute brine, dried over Na₂SO₄ and concentrated in vacuo.

Work-up 2: The excess amine was removed by distillation and the residue dissolved in CH₂Cl₂ or EtOAc, washed with aqueous NaHCO₃ and dilute brine, dried over Na₂SO₄ and concentrated in vacuo.

The residue was either chromatographed over silica gel, eluting with methanol or methanol-methylene chloride mixtures and/or recrystallized from ethyl acetate, methanol, ethanol-ethyl acetate, diethyl ether-light petroleum ether, or the like, to yield the product. Example 1 hereinabove exemplifies this procedure.

EXAMPLE 8

8-Chloro-N-methyl-β,6-diphenyl-4H-[1,2,4]triazolo[4,3-a][1,4]benzodiazepine-1-ethanamine A mixture of the quaternary ammonium salt from Example 1, Part A, hereinabove (7 mmole) and 50 ml of methylamine is sealed in a pressure reaction vessel and heated in an oil bath at 100° for 24 hours and then allowed to cool. The reaction mixture is removed from the pressure vessel and concentrated under a stream of nitrogen. The residue is treated with a 1:1 (v/v) mixture of ethyl acetate and methylene dichloride. Concentration of this mixture gives the titled product which is further purified by recrystallization.

EXAMPLE 9

8-Iodo-N,N-dimethyl-6-phenyl-4H-[1,2,4]triazolo[4,3-a][1,4]benzodiazepine-1-ethanamine The iodothione prepared as described in Example 6, Part B, hereinabove is reacted with acetic aid hydrazide by the method described in Example 1 of Hester, Jr., U.S. Pat. No. 3,987,052 to produce 8-iodo-1-methyl-6-phenyl-4H-[1,2,4]triazolo[4,3-a][1,4]benzodiazepine.

A stirred solution of the intermediate thus produced (0.01 mole) in dry DMF (50 ml) is cooled in an ice bath under nitrogen and treated successively with N,N,N′,N′-tetramethyldiaminomethane (0.012 mole) and dropwise with acetyl chloride (0.013 mole). The cooling is maintained for two hours, and the mixture is then poured into a mixture of ice and saturated sodium bicarbonate. The mixture is saturated with sodium chloride and extracted with chloroform. The extracts are washed with brine, dried over anhydrous sodium sulfate and concentrated to remove the solvent using xylene and toluene to help remove the residual DMF to give the titled product, which is further purified by conversion to a crystalline acid addition salt.

EXAMPLE 10

Ten thousand hard gelatin capsules for oral use, each containing 25 mg of 8-chloro-N,N-dimethyl-β,6-diphenyl-4H-[1,2,4]triazolo-[4,3-a][1,4]benzodiazepine-1-ethanamine and 2.5 mg of minoxidil are prepared from the following ingredients:

| | Gm. |
|---|---|
| 8-chloro-N,N—dimethyl-β,6-diphenyl-4H—[1,2,4]-triazolo[4,3-a][1,4]-benzodiazepine-1-ethanamine | 250 |
| Minoxidil | 25 |
| Starch | 350 |
| Talc | 250 |
| Calcium stearate | 150 |

| -continued | |
|---|---|
| | Gm. |
| Lactose | 1750 |

One capsule one to four times a day is useful in the treatment of hypertension.

EXAMPLE 11

Ten thousand tablets for oral use, each containing 25 mg of 8-iodo-N,N-dimethyl-β,6-diphenyl-4H-[1,2,4]triazolo[4,3-a][1,4]benzodiazepine-1-ethanamine are prepared from the following ingredients:

| | Gm. |
|---|---|
| 8-iodo-N,N—dimethyl-β,6-diphenyl-4H—[1,2,4]triazolo-[4,3-a][1,4]benzodiazepine-1-ethanamine | 250 |
| Lactose | 1200 |
| Corn starch | 500 |
| Talc | 500 |
| Calcium stearate | 25 |

The powdered ingredients are thoroughly mixed and slugged. The slugs are broken into granules which are then compressed into tablets. To induce diuresis in adult humans, one tablet is administered one to four times daily.

FORMULAS

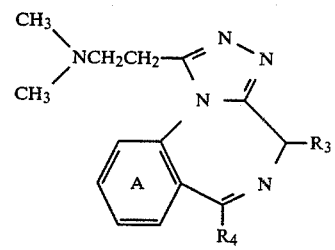

I

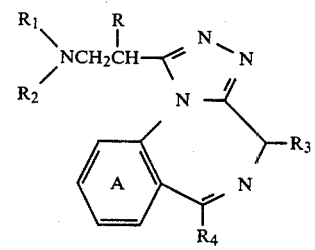

II

We claim:

1. A process for inducing diuresis in a warm-blooded animal patient which comprises administering to such patient a safe, non-toxic, effective amount of a compound of the Formula I

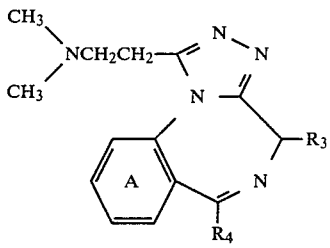

wherein
- $R_3$ is hydrogen or $C_1$ to $C_3$-alkyl;
- $R_4$ is phenyl or 2-, 3-, or 4-pyridinyl;
- ring A is substituted by one or more fluorine, bromine, iodine, $C_1$ to $C_3$-alkyl, hydroxy, $C_1$ to $C_3$-alkyloxy, $C_1$ to $C_3$-alkylthio, amino, $C_1$ to $C_3$-alkylamino, di($C_1$ to $C_3$-alkyl)amino, trifluoromethyl, or nitro;

or of a compound of the Formula II

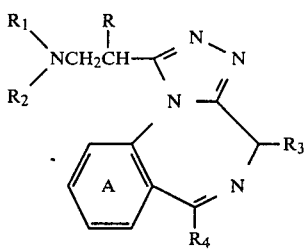

wherein
- R is phenyl substituted by zero to two methoxy or orthochlorine groups;
- $R_1$ and $R_2$ are independently hydrogen or $C_1$ to $C_3$-alkyl;
- $R_3$ is hydrogen or $C_1$ to $C_3$-alkyl;
- $R_4$ is phenyl or 2-, 3-, or 4-pyridinyl;
- ring A is substituted by one or more fluorine, chlorine, bromine, iodine, $C_1$ to $C_3$-alkyl, hydroxy, $C_1$ to $C_3$-alkyloxy, $C_1$ to $C_3$-alkylthio, amino, $C_1$ to $C_3$-alkylamino, di($C_1$ to $C_3$-alkyl)amino, trifluoromethyl, or nitro;

or a pharmaceutically acceptable salt thereof.

2. A process according to claim 1 wherein said patient is treated with 8-chloro-N,N-dimethyl-β,6-diphenyl-4H-[1,2,4]triazolo[4,3-a][1,4]benzodiazepine-1-ethaneamine, or a pharmaceutically acceptable salt thereof.

3. A process according to claim 1 wherein said patient is treated with 8-bromo-N,N-dimethyl-6-phenyl-4H-[1,2,4]triazolo[4,3-a][1,4]benzodiazepine-1-ethanamine, or a pharmaceutically acceptable salt thereof.

4. A process according to claim 1 wherein said patient is treated with 8-bromo-N,N-dimethyl-β,6-diphenyl-4H-s-triazolo[4,3-a][1,4]benzodiazepine-1-ethanamine, or a pharmaceutically acceptable salt thereof.

5. A process according to claim 1 wherein said patient is treated with 8-chloro-β,6-diphenyl-4H-[1,2,4]triazolo[4,3-a][1,4]benzodiazepine-1-ethanamine, or a pharmaceutically acceptable salt thereof.

6. A process according to claim 1 wherein said patient is treated with N,N-dimethyl-8-(methylthio)-β,6-diphenyl-4H-[1,2,4]triazolo[4,3-a][1,4]benzodiazepine-1-ethanamine, or a pharmaceutically acceptable salt thereof.

7. A process according to claim 1 wherein said patient is treated with 8-chloro-β-(3-methoxyphenyl)-N,N-dimethyl-6-phenyl-4H-[1,2,4]triazolo[4,3-a][1,4]benzodiazepine-1-ethanamine, or a pharmacologically acceptable salt thereof.

8. A process according to claim 1 wherein said patient is treated with 8-chloro-β-(2-chlorophenyl)-N,N-dimethyl-6-phenyl-4H-[1,2,4]triazolo[4,3-a][1,4]benzodiazepine-1-ethanamine, or a pharmacologically acceptable salt thereof.

9. A process according to claim 1 wherein said patient is treated with 8-chloro-N,N,4-trimethyl-β,6-diphenyl-4H-[1,2,4]triazolo[4,3-a][1,4]benzodiazepine-1-ethanamine, or a pharmacologically acceptable salt thereof.

10. A process according to claim 1 wherein said patient is treated with 8-chloro-β-(4-methoxyphenyl)-N,N-dimethyl-6-phenyl-4H-[1,2,4]triazolo[4,3-a][1,4]benzodiazepine-1-ethanamine, or a pharmacologically acceptable salt thereof.

11. A process according to claim 1 wherein said patient is treated with 8-iodo-N,N-dimethyl-β-6-diphenyl-4H-[1,2,4]triazolo[4,3-a][1,4]benzodiazepine-1-ethanamine, or a pharmacologically acceptable salt thereof.

12. A process according to claim 1 wherein said patient is treated with 8-chloro-β-(2-methoxyphenyl)-N,N-dimethyl-6-phenyl-4H-[1,2,4]triazolo[4,3-a][1,4]benzodiazepine-1-ethanamine, or a pharmacologically acceptable salt thereof.

13. A process according to claim 1 wherein said patient is treated with 8-bromo-N,N-dimethyl-6-(2-pyridinyl)-4H-[1,2,4]triazolo[4,3-a][1,4]benzodiazepine-1-ethanamine, or a pharmacologically acceptable salt thereof.

14. A method for treating hypertension in a warm-blooded animal patient which comprises concomittantly administering to said patient an amount effective to induce diuresis of a compound of Formula I or II of claim 1 and an antihypertensive agent.

15. A method according to claim 14 wherein the compound of Formula I or II used to effect diuresis is a compound selected from the group consisting of 8-chloro-N,N-dimethyl-β,6-diphenyl-4H-[1,2,4]triazolo[4,3-a][1,4]benzodiazepine-1-ethanamine, 8-bromo-N,N-dimethyl-6-phenyl-4H-[1,2,4]triazolo[4,3-a][1,4]benzodiazepine-1-ethanamine, 8-bromo-N,N-dimethyl-β,6-diphenyl-4H-s-triazolo[4,3-a][1,4]benzodiazepine-1-ethanamine, 8-chloro-β,6-diphenyl-4H-[1,2,4]triazolo[4,3-a][1,4]benzodiazepine-1-ethanamine, N,N-dimethyl-8-(methylthio)-β,6-diphenyl-4H-[1,2,4]triazolo[4,3-a][1,4]benzodiazepine-1-ethanamine, 8-chloro-β-(3-methoxyphenyl)-N,N-dimethyl-6-phenyl-4H-[1,2,4]triazolo[4,3-a][1,4]benzodiazepine-1-ethanamine, 8-chloro-β-(2-chlorophenyl)-N,N-dimethyl-6-phenyl-4H-[1,2,4]triazolo[4,3-a][1,4]benzodiazepine-1-ethanamine, 8-chloro-N,N,4-trimethyl-β,6-diphenyl-4H-[1,2,4]triazolo[4,3-a][1,4]benzodiazepine-1-ethanamine, 8-chloro-β-(4-methoxyphenyl)-N,N-dimethyl-6-phenyl-4H-[1,2,4]triazolo[4,3-a][1,4]benzodiazepine-1-ethanamine, 8-iodo-N,N-dimethyl-β,6-diphenyl-4H-[1,2,4]triazolo[4,3-a][1,4]benzodiazepine-1-ethanamine, 8-chloro-β-(2-methoxyphenyl)-N,N-dimethyl-6-phenyl-4H-[1,2,4]triazolo[4,3-a][1,4]benzodiazepine-1-ethanamine, 8-bromo-N,N-dimethyl-6-(2-pyridinyl)-4H-[1,2,4]triazolo[4,3-a][1,4]benzodiazepine-1-ethanamine, or a pharmacologically acceptable salt thereof.

16. A method for treating hypertension in a warm-blooded animal patient which comprises administering to said patient an amount effective to lower blood pressure of a compound of Formula I or II of claim 1.

* * * * *